(12) United States Patent
Koizumi (10) Patent No.: US 10,288,304 B2
(45) Date of Patent: May 14, 2019

(54) SYSTEMS AND METHODS FOR ADJUSTING THE ATMOSPHERE OF EXERCISE STUDIOS

(71) Applicant: Shota Koizumi, Tokyo, PA (US)

(72) Inventor: Shota Koizumi, Tokyo, PA (US)

( * ) Notice: Subject to any disclaimer, the term of this patent is extended or adjusted under 35 U.S.C. 154(b) by 162 days.

(21) Appl. No.: 15/549,278

(22) PCT Filed: Jan. 22, 2016

(86) PCT No.: PCT/JP2016/051927
§ 371 (c)(1),
(2) Date: Aug. 7, 2017

(87) PCT Pub. No.: WO2017/051546
PCT Pub. Date: Mar. 30, 2017

(65) Prior Publication Data
US 2018/0087788 A1    Mar. 29, 2018

(30) Foreign Application Priority Data

Sep. 24, 2015 (JP) .................................. 2015-187178

(51) Int. Cl.
| | |
|---|---|
| *F24F 6/18* | (2006.01) |
| *B01F 3/04* | (2006.01) |
| *A61H 33/10* | (2006.01) |
| *E04F 15/18* | (2006.01) |
| *E04H 3/14* | (2006.01) |
| *A61M 16/00* | (2006.01) |
| *F24F 6/02* | (2006.01) |
| *F24F 6/10* | (2006.01) |
| *F24F 110/10* | (2018.01) |
| *F24F 110/20* | (2018.01) |

(52) U.S. Cl.
CPC ............... *F24F 6/18* (2013.01); *A61H 33/10* (2013.01); *B01F 3/04* (2013.01); *E04F 15/18* (2013.01); *E04H 3/14* (2013.01); *A61M 16/022* (2017.08); *F24F 6/025* (2013.01); *F24F 6/105* (2013.01); *F24F 2110/10* (2018.01); *F24F 2110/20* (2018.01); *F24F 2221/08* (2013.01)

(58) Field of Classification Search
CPC ............... F24F 6/18; B01F 3/04; A61H 33/10
USPC .......................................................... 261/26
See application file for complete search history.

(56) References Cited

FOREIGN PATENT DOCUMENTS

JP           2000060933 A  *  2/2000  ............. A61H 33/10

* cited by examiner

*Primary Examiner* — Robert A Hopkins
(74) *Attorney, Agent, or Firm* — Studebaker & Brackett PC (57) ABSTRACT

An atmosphere adjustment system includes a steam supply unit and a control unit. The steam supply unit has: a layered structure including a first lava sand layer, a mineral layer, a second lava sand layer and a lava plate, which are stacked in this order from the bottom; a heater arranged under the first lava sand layer; and a water supply pipe arranged between the first lava sand layer and the mineral layer. The control unit is able to adjust the temperature of the second lava sand layer at 60° C. or higher and 80° C. or lower by controlling at least one of the amount of water discharged through the water supply pipe or the temperature of the heater.

11 Claims, 6 Drawing Sheets

SYSTEMS AND METHODS FOR ADJUSTING THE ATMOSPHERE OF EXERCISE STUDIOS

TECHNICAL FIELD

The present invention relates to systems and methods for adjusting the atmosphere of exercise studios.

BACKGROUND ART

Exercise studios, such as yoga studios and stretching studios, are used for the maintenance and advancement of health. The atmosphere, e.g., temperature, humidity, etc., of such exercise studios is typically adjusted by using common heating and cooling equipment.

SUMMARY

Technical Problem

The inventors of the present invention are considering increasing the effects of exercise by doing exercise while delivering heat deep into the body. However, with the use of common heating and cooling equipment, it is difficult to apply heat deep into the body and the effect of exercise cannot be sufficiently increased.

In view of the above, the inventors of the present invention are considering placing, on the floor of the studio, a steam supply unit that supplies steam containing minerals into the studio together with the emission of far-infrared radiation. More specifically, the steam supply unit has: a layered structure including a first lava sand layer, a mineral layer, a second lava sand layer and a lava plate, which are stacked in this order from the bottom; a heater provided under the first lava sand layer; and a water supply pipe provided between the first lava sand layer and the mineral layer, with such steam supply unit being configured to discharge water to the first lava sand layer through the water supply pipe and to allow the discharged water to evaporate with the use of the heater so that the resulting steam passes through the mineral layer, then accumulates in the second lava sand layer, and is finally discharged into the studio through the lava plate.

By using such steam supply unit, warm steam that has passed through the mineral layer so as to contain minerals therein is discharged into the studio and, furthermore, far-infrared radiation is emitted from the lava layers, so that the atmosphere of the studio is accordingly adjusted. This configuration enables users to exercise while heat is applied deep into their bodies.

In the above configuration, the second lava sand layer, which is located at an upper layer of the steam supply unit, is likely to be in a hot and humid condition due to a temperature decrease and such second lava sand layer thus has the risk of bacterial growth therein. If the second lava sand layer includes bacteria, steam containing bacteria may be discharged into the studio. Accordingly, it becomes necessary to frequently conduct cleaning, replacement and other maintenance operations for the second lava sand layer and its surroundings in the steam supply unit, which requires considerable cost.

The present invention has been made in view of the above circumstances. It is an object of the present invention to provide systems and methods for adjusting the atmosphere of exercise studios, configured to adjust the atmosphere of a studio by using the above-mentioned steam supply unit wherein the growth of bacteria in the second lava sand layer, which would otherwise occur in the adjustment, can be suppressed.

Solution to Problem

The inventors of the present invention have found, as a result of intensive studies, that the growth of bacteria can be suppressed by adjusting the temperature of the second lava sand layer in the steam supply unit within a specific temperature range so as to accordingly sterilize the second lava sand layer, and have completed the present invention.

That is, the present invention includes the following aspects:

(1) A system for adjusting an atmosphere of an exercise studio, the system comprising: a steam supply unit which has a layered structure including a first lava sand layer, a mineral layer, a second lava sand layer and a lava plate, which are stacked in this order from the bottom, a heater provided under the first lava sand layer, and a water supply pipe provided between the first lava sand layer and the mineral layer; and a control unit which is able to adjust the temperature of the second lava sand layer at 60° C. or higher and 80° C. or lower by controlling at least one of the amount of water discharged through the water supply pipe or the temperature of the heater, wherein the steam supply unit is placed on the floor of the studio, and wherein the steam supply unit is configured to discharge water to the first lava sand layer through the water supply pipe and to allow the discharged water to evaporate with the heater so that the resulting steam passes through the mineral layer, accumulates in the second lava sand layer, and is then discharged into the studio through the lava plate.

(2) The system for adjusting an atmosphere of an exercise studio as set out in (1) above, wherein the lava plate of the steam supply unit has a first lava plate having relatively high air permeability and a second lava plate having relatively low air permeability.

(3) The system for adjusting an atmosphere of an exercise studio as set out in (2) above, wherein the first lava plate and the second lava plate are each arranged so as to occupy an almost equal proportion of a floor surface of the studio.

(4) The system for adjusting an atmosphere of an exercise studio as set out in any of (1) to (3) above, wherein the second lava sand layer is formed so as to be thicker than the first lava sand layer.

(5) The system for adjusting an atmosphere of an exercise studio as set out in any of (1) to (4) above, wherein the second lava sand layer has a lower layer which is made of lava sand with relatively large particle sizes and an upper layer which is made of lava sand with relatively small particle sizes.

(6) The system for adjusting an atmosphere of an exercise studio as set out in any of (1) to (5) above, wherein the second lava sand layer has a thickness of 5 mm or more and 15 mm or less.

(7) The system for adjusting an atmosphere of an exercise studio as set out in any of (1) to (6) above, wherein the first lava sand layer has a lower layer which is made of lava sand with relatively small particle sizes and an upper layer which is made of lava sand with relatively large particle sizes.

(8) The system for adjusting an atmosphere of an exercise studio as set out in any of (1) to (7) above, wherein the thickness ratio of the second lava sand layer to the lava plate is set to 1:2 or greater and 1:4 or smaller.

(9) The system for adjusting an atmosphere of an exercise studio as set out in any of (1) to (8) above, wherein the mineral layer includes at least one kind of mineral selected from quartz, rose quartz, tourmaline, tortoiseshell, agate tiger's eye, malachite, rutile quartz, pyrite, amazonite, turquoise, lapis lazuli, tumbled rock, and tumbled hawk's eye.

(10) The system for adjusting an atmosphere of an exercise studio as set out in any of (1) to (9) above, wherein the water supply pipe is arranged in a predetermined pattern across the surface of the floor of the studio and the heater is arranged directly under the water supply pipe.

(11) A method for adjusting an atmosphere of an exercise studio, the method comprising: placing a steam supply unit on the floor of a studio, wherein the steam supply unit has a layered structure including a first lava sand layer, a mineral layer, a second lava sand layer and a lava plate, which are stacked in this order from the bottom, a heater provided under the first lava sand layer, and a water supply pipe provided between the first lava sand layer and the mineral layer; discharging water to the first lava sand layer through the water supply pipe; using the heater so that the discharged water evaporates; allowing the resulting steam to pass through the mineral layer, then accumulate in the second lava sand layer, and thereafter be discharged into the studio through the lava plate, so as to adjust an atmosphere of the studio, wherein, in the adjustment, at least one of the amount of water discharged through the water supply pipe or the temperature of the heater is controlled so that the second lava sand layer is at a temperature of 60° C. or higher and 80° C. or lower.

Advantageous Effects of Invention

According to the present invention, when adjusting the atmosphere of a studio by using a steam supply unit, the growth of bacteria in the second lava sand layer can be suppressed, and therefore, the frequency of maintenance operations can be reduced, which leads to the reduction of cost.

DESCRIPTION OF EMBODIMENTS

Hereinafter, preferred embodiments of the present invention will be described with reference to the attached drawings. It should be noted that the same elements will be given the same reference numerals and any repetitive explanation will be omitted. Unless otherwise specified, the positional relationships, such as up-and-down and left-and-right relationships, are based on those shown in the drawings. The various dimensional ratios shown in the drawings are not limited to those shown in the drawings. In addition, the below embodiments are just examples for describing the present invention and the present invention is not limited to the described embodiments.

Figure 1:
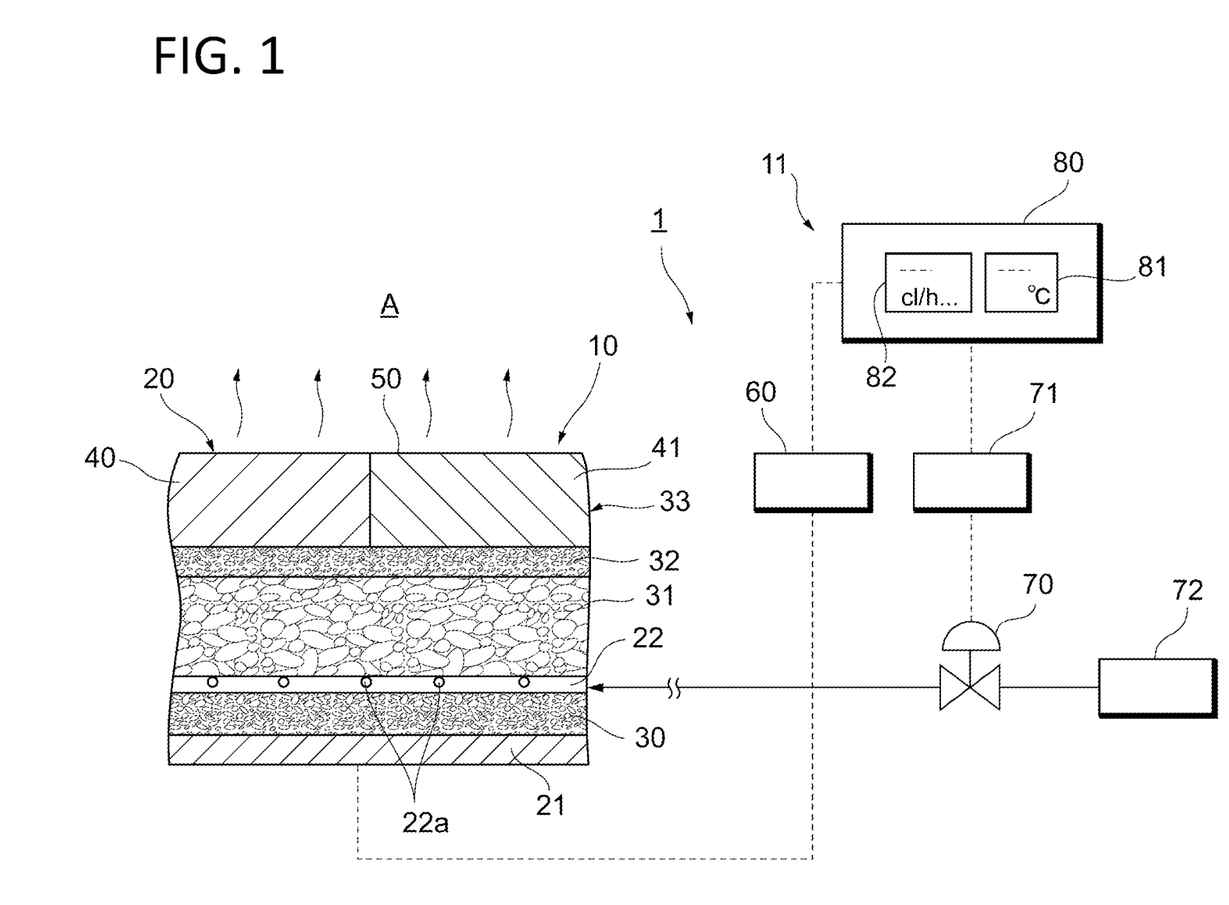
FIG. 1 is a schematic illustration showing an example of the configuration of an atmosphere adjustment system.
Figure 2:
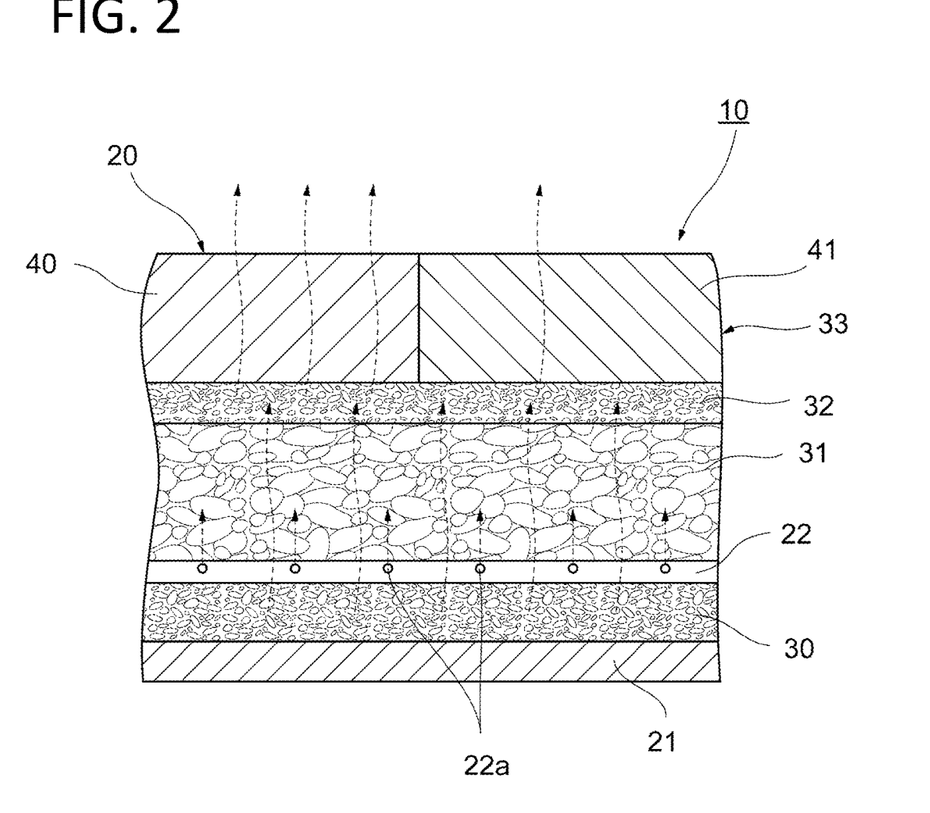
FIG. 2 is an illustration for explaining an example of a layered structure of a steam supply unit.

FIG. 1 is a schematic illustration showing the outline of the configuration of an atmosphere adjustment system 1 for exercise studios according to the present embodiment. FIG. 2 is a schematic illustration showing an example of the configuration of a steam supply unit 10 used in the atmosphere adjustment system 1. The term "exercise studio," as used herein, includes all types of studios for doing exercise, and examples thereof include yoga studios, stretching studios, dance studios, Pilates studios, aerobic exercise studios, studios for dieting, and studios for practicing meditation or zazen.

As illustrated in FIG. 1, the atmosphere adjustment system 1 has, for example, a steam supply unit 10 and a control unit 11.

The steam supply unit 10 is placed on the floor of a studio A, and has a layered structure 20 comprised of a plurality of layers, a heater 21, and a water supply pipe 22.

As shown in FIG. 2, the layered structure 20 includes, for example, a first lava sand layer 30, a mineral layer 31, a second lava sand layer 32 and a lava plate 33, which are arranged in this order from the bottom.

Figure 3:
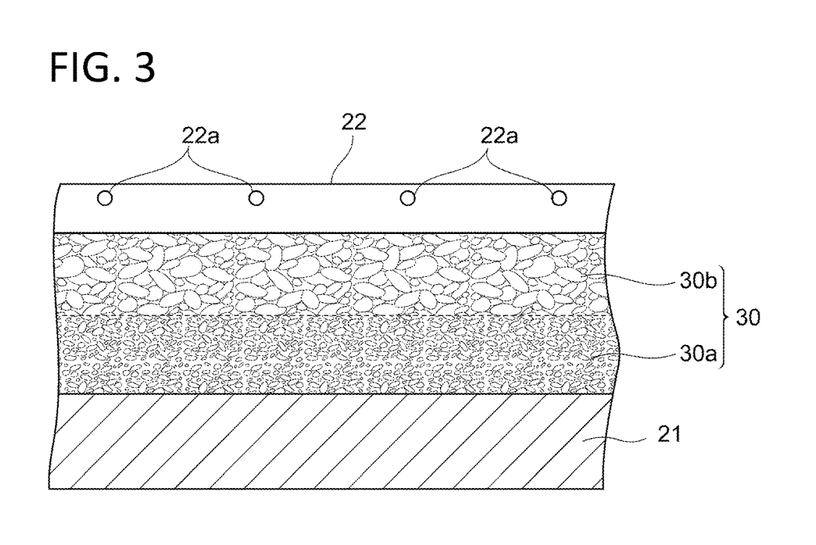
FIG. 3 is an enlarged schematic view of a first lava sand layer.

The first lava sand layer 30 is made of, for example, lava rock, which is finely pulverized and then sieved into particles of almost equal sizes. The first lava sand layer 30 has a thickness of, for example, 10 mm or more and 30 mm or less, and preferably has a thickness of about 20 mm. For example, the first lava sand layer 30 has a lower layer 30a which is made of lava sand having relatively small particle sizes and an upper layer 30b which is made of sand lava having relatively large particle sizes, as shown in FIG. 3. The particle size of the lower layer 30a is, for example, about 2 mm or less and the particle size of the upper layer 30b is, for example, about 5 mm. It should be noted here that the lower layer 30a and the upper layer 30b do not have to be strictly separated, and the first lava sand layer 30 may be prepared by arranging smaller particles of lava sand on the heater 21 to form a lower layer 30a and then arranging larger particles of lava sand on the obtained lower layer 30a to form an upper layer 30b.

The mineral layer 31 shown in FIG. 2 is comprised of, for example, at least one kind of ore. The mineral layer 31 includes, for example, at least one kind, and preferably at least five kinds of ore selected from quartz, rose quartz, tourmaline, tortoiseshell, agate tiger's eye, malachite, rutile quartz, pyrite, amazonite, turquoise, lapis lazuli, tumbled rock, and tumbled hawk's eye. The ore used for the mineral layer 31 has a size of, for example, about 3 cm or more and 10 cm or less. The mineral layer 31 has a thickness of, for example, 30 mm to 50 mm, and preferably has a thickness of about 40 mm. The mineral layer 31 may include substances other than ores.

Figure 4:
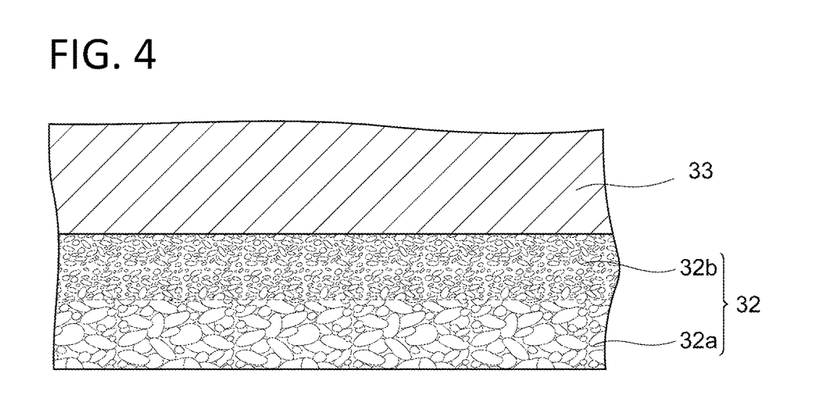
FIG. 4 is an enlarged schematic view of a second lava sand layer.

The second lava sand layer 32 is made of, for example, lava rock, which is finely pulverized and then sieved into particles of almost equal sizes. The second lava sand layer 32 has a thickness of, for example, 5 mm or more and 15 mm or less, and preferably has a thickness of about 10 mm. In order for steam to accumulate in the second lava sand layer 32, the second lava sand layer 32 is formed so as to be thicker than the first lava sand layer 30. For example, the second lava sand layer 32 has a lower layer 32a which is made of lava sand with relatively large particle sizes and an upper layer 32b which is made of lava sand with relatively small particle sizes, as shown in FIG. 4. The particle size of the lower layer 32a is, for example, about 5 mm and the particle size of the upper layer 32b is, for example, about 2 mm or less.

Figure 5:
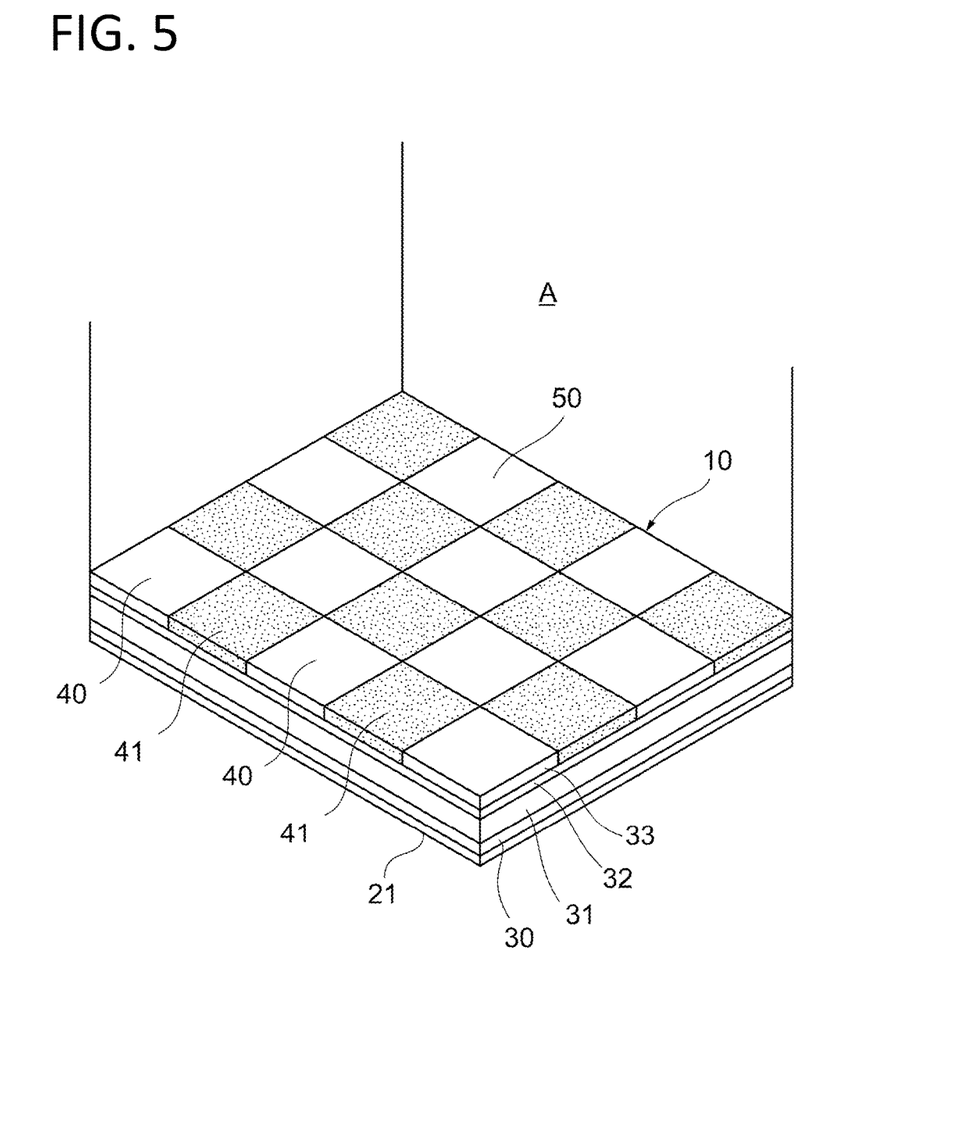
FIG. 5 is a schematic illustration showing the structure of the floor of a studio.

The lava plate 33 shown in FIGS. 1 and 2 has a thickness of, for example, 20 mm or more and 40 mm or less, and preferably has a thickness of about 30 mm. The ratio of the thickness of the second lava sand layer 32 to the thickness of the lava plate 33 is set to 1:2 or more and 1:4 or less. The lava plate 33 includes, for example, two types of plates—a first lava plate 40 having relatively low air permeability and a second lave plate 41 having relatively high air permeability. The first lava plate 40 is made of lava rock having high rock density and low porosity taken out from the third layer from the ground surface. The second lava plate 41 is made of lava rock having low rock density and high porosity taken out from the second layer from the ground surface. For example, as shown in FIG. 5, the first and second lava plates 40 and 41 are each processed in a square of the same size and laid on the floor surface 50 of the studio A so as to occupy an almost equal proportion of the surface. For example, the first and second lava plates 40 and 41 may be arranged alternately to form a checkerboard pattern.

The heater 21 shown in FIGS. 1 and 2 is provided under the first lava sand layer 30. For example, the heater 21 may be arranged in a line having a width of about 5 cm, or in a sheet-form. Upon receiving power supply the heater 21 is able to generate heat at 100° C. or higher. The water supply pipe 22 is provided between the first lava sand layer 30 and the mineral layer 31 and communicates with a water supply 72, e.g., a water tap, as shown in FIG. 1.

Figure 6:
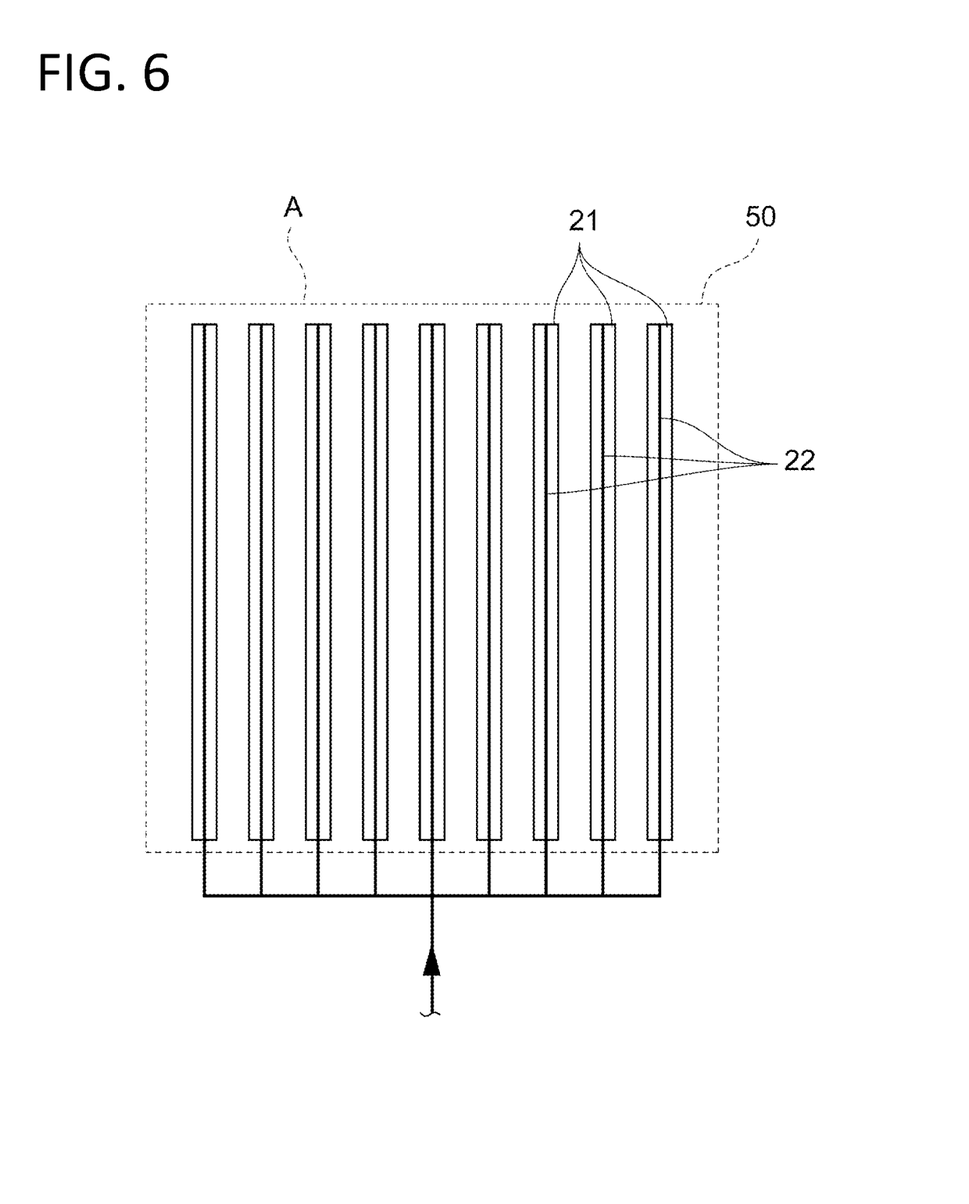
FIG. 6 is an illustration for explaining the arrangement pattern of a water supply pipe and a heater when seen from the top.

The water supply pipe 22 is arranged, for example, in a predetermined pattern, e.g., a pattern in which several water supply pipes 22 are placed in parallel, across the floor surface 50 of the studio A, as shown in FIG. 6. As illustrated in FIGS. 1 and 2, the water supply pipe 22 is, for example, a metal pipe having a diameter of about 10 mm with a plurality of water supply holes 22a formed along the pipe. The water supply holes 22a are formed, for example, in the upper half of the water supply pipe 22 so as to face upward.

As shown in FIG. 1, the control unit 11 is configured to include, for example, a heater controller 60 that controls the amount of power supply to the heater 21, a valve 70 capable of controlling the amount of water supply through the water supply pipe 22, a valve controller 71 that controls the amount or time of opening of the valve 70, and an overall controller 80 that performs control for the heater controller 60 and the valve controller 71. The overall controller 80 is, for example, a computer and it includes, for example, a temperature setting input part 81 with which a temperature set value for the heater 21, etc., can be input manually and a water supply setting input part 82 with which a set value for the amount of water supply through the water supply pipe 22, etc., can be input manually. The overall controller 80 can control the temperature of the heater 21 with the heater controller 60 by, for example, controlling the heater controller 60 based on the temperature set value that has been input to the temperature setting input part 81. Further, the overall controller 80 can control the amount of water supply through the water supply pipe 22 by, for example, controlling the valve controller 71 based on the water supply set value that has been input to the water supply setting input part 82 so that the amount or time of opening of the value 70 is controlled by the valve controller 71. In this manner, the control unit 11 controls at least one of the amount of water discharged through the water supply pipe 22 or the temperature of the heater 21, and can consequently adjust the temperature of the second lava sand layer 32 to 60° C. or higher and 80° C. or lower.

When the above-described atmosphere adjustment system 1 operates to adjust the atmosphere of the studio A, water flows through the water supply pipe 22 at a flow rate (e.g., 2 to 4 cl/h) which is set by the control unit 11, and the water is discharged through the water supply holes 22a of the water supply pipe 22 in the steam supply unit 10. Further, the heater 21 is controlled at a temperature (e.g., about 110° C.) which is set by the control unit 11. In the steam supply unit 10, water is discharged through the water supply pipe 22 into the first lava sand layer 30, where the water evaporates due to the heater 21 and the resulting steam goes up through the mineral layer 31. When the steam goes up, minerals contained in the mineral layer 31 attach to water molecules in the steam. It is preferable for the steam to have a temperature of, for example, about 40° C. to 75° C. when it passes through the mineral layer 31. The steam, after passing through the mineral layer 31, accumulates in the second lava sand layer 32. At that time, heat is also accumulated together with the steam in the second lava sand layer 32, so that the second lava sand layer 32 has a temperature of 60° C. or higher and 80° C. or lower, and preferably has a temperature of about 70° C. The steam in the second lava sand layer 32 is then discharged into the studio A through the lava plate 33 (mainly through the first lava plate 40). With such discharged steam, the temperature of the surface of the lava plate 33, which serves as the floor surface 50, is about 43° C. to 44° C., the humidity of the studio A is 60% to 70%, and the temperature of the studio A is about 38° C. to 40° C. In addition, the heated lava layers 30 and 32 as well as the lava plate 33 emit far-infrared radiation into the studio A. As a result, the interior of the studio A has a mineral-containing steam atmosphere with far-infrared radiation, i.e., the studio A is adjusted to have a predetermined atmosphere with a predetermined temperature and humidity.

According to the present embodiment, with the use of the steam supply unit 10, steam that has passed through the mineral layer 31 to contain, for example, minerals therein is discharged into the studio A and far-infrared radiation is also emitted from the first lava sand layer 30, the second lava sand layer 32 and the lava plate 33 into the studio A, so that the atmosphere in the studio A is adjusted to a predetermined temperature and humidity, and this consequently enables users to exercise while heat is applied deep into their bodies. Thus, the effect of exercise can be increased. Furthermore, the temperature of the second lava sand layer 32 can be adjusted to 60° C. or higher and 80° C. or lower by using the control unit 11 to control at least one of the amount of water discharged through the water supply pipe 22 or the temperature of the heater 21, and therefore, the second lava sand layer 32 is sterilized. As a result, the growth of bacteria in the second lava sand layer 32, which would otherwise occur when adjusting the atmosphere of the studio A by using the steam supply unit 10, can be suppressed. In this manner, the present embodiment can supply bacteria-free steam within the studio, and can also decrease maintenance frequency for the steam supply unit 10 to accordingly achieve cost reduction. It should be noted here that when the temperature of the second lava sand layer 32 is lower than 60° C., a sufficient level of sterilization is unable to be performed; whereas, when the temperature of the second lava sand layer 32 exceeds 80° C., the temperature of the surface of the lava plate 33 and the surroundings thereof becomes excessively high and is not suited for exercise studios.

Since the lava plate 33 of the steam supply unit 10 has a first lava plate 40 having relatively high air permeability and a second lava plate 41 having relatively low air permeability, this configuration enables steam to be accumulated appropriately in the second lava sand layer 32 and, at the same time, enables the discharge of an appropriate portion of such steam into the studio A through the lava plate 33.

Since the first lava plate 40 and the second lava plate 41 are arranged on the floor surface 50 of the studio at an almost equal proportion of the surface, such configuration ensures good balance between the accumulation of steam in the second lava sand layer 32 and the discharge of steam through the lava plate 33. As a result, the temperature of the second lava sand layer 32 can be adjusted appropriately to 60° C. or higher and 80° C. or lower.

Since the second lava sand layer 32 is formed so as to be thicker than the first lava sand layer 30, the second lava sand layer 32 has an increased capacity for accumulating steam and an increased capacity for accumulating heat, which makes it easier to maintain the temperature of the second lava sand layer 32 at 60° C. or higher and 80° C. or lower.

Since the second lava sand layer 32 has a thickness of 5 mm or more and 15 mm or less, such thickness ensures a suitable capacity for accumulating steam and a capacity for accumulating heat, which makes it easier to maintain the temperature of the second lava sand layer 32 at 60° C. or higher and 80° C. or lower.

Since the second lava sand layer 32 has a lower layer 32a which is made of lava sand with relatively large particle sizes and an upper layer 32b which is made of lava sand with relatively small particle sizes, the lower layer 32a can serve to maintain the boundary with the mineral layer 31, while the upper layer 32b can serve to achieve flat placement of the lava plate 33 thereon.

Since the first lava sand layer 30 has a lower layer 30a which is made of lava sand with relatively small particle sizes and an upper layer 30b which is made of lava sand with relatively large particle sizes, this configuration enables water in the water supply pipe 22 to be sufficiently spread and held within the lower layer 30a. As a result, by using the heater 21, steam can be generated efficiently and evenly throughout the floor surface and such generated steam can be supplied within the studio A.

Since the ratio of the thickness of the second lava sand layer 32 to the thickness of the lava plate 33 is set to 1:2 or more and 1:4 or less, this configuration enables the temperature of the steam to be sufficiently decreased when the steam is passing through the lava plate 33 after the temperature has been adjusted to 60° or higher and 80° C. or lower in the second lava sand layer 32, and the surface temperature of the lava plate 33 (i.e., the temperature of the floor surface) can be accordingly adjusted to a suitable temperature for exercise studios.

Since the mineral layer 31 includes at least one kind of mineral selected from quartz, rose quartz, tourmaline, tortoiseshell, agate tiger's eye, malachite, rutile quartz, pyrite, amazonite, turquoise, lapis lazuli, tumbled rock, and tumbled hawk's eye, minerals are attached to the steam so as to, for example, facilitate the sweating of the human body, and the effect of exercise can be further enhanced.

Since the water supply pipe 22 is arranged in a predetermined pattern across the floor surface 50 of the studio and the heater 21 is arranged directly under such water supply pipe 22, this configuration enables water discharged through the water supply pipe 22 to evaporate in an efficient manner.

Preferred embodiments of the present invention have been described above with reference to the attached drawings. The present invention, however, is not limited to the described examples. A person skilled in the art could obviously think of various modifications and alterations without departing from the idea specified in the scope of the claims and it should be appreciated that such modifications and alterations would obviously be encompassed within the technical scope of the present invention.

Figure 7:
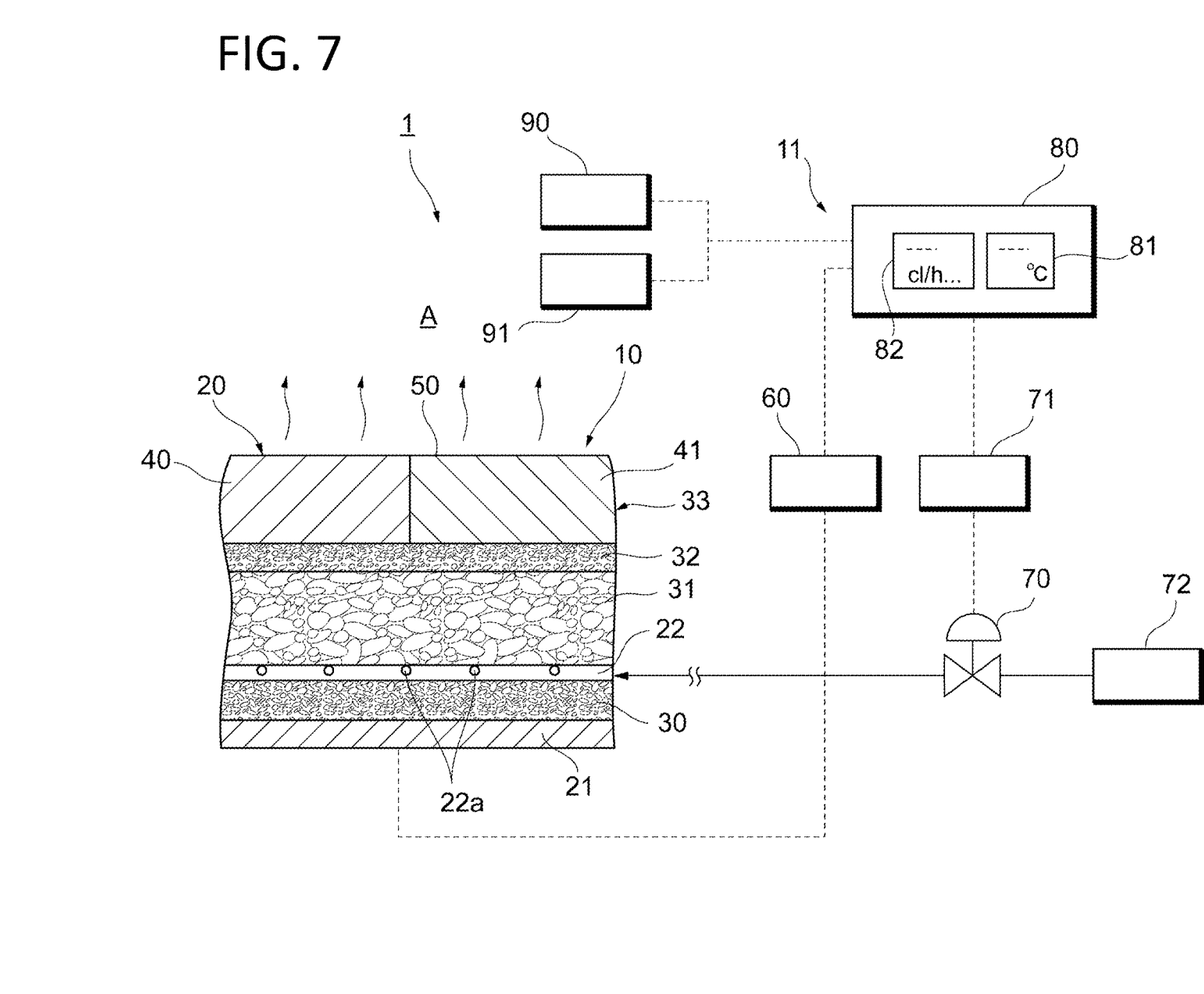
FIG. 7 is a schematic illustration showing another example of the configuration of an atmosphere adjustment system.

For example, the configuration of the control unit 11 is not limited to that set forth in the above-described embodiment, and other configurations may be employed. For example, although the control unit 11 in the above embodiment adjusts the flow rate in the water supply pipe 22 by using the valve 70, such adjustment may instead be performed by using a pump. Further, although the temperature of the heater 21 and the flow rate in the water supply pipe 22 are set manually by the user in the above-described embodiment, for example, the control unit 11 may automatically control the heater 21 and the valve 70 so that the temperature and humidity in the studio A correspond to a specific set temperature and set humidity. In such a case, the control unit 11 may further include, for example, a temperature sensor 90 and a humidity sensor 91 which are placed in the studio A as shown in FIG. 7 and the overall controller 80 may perform feedback control for the temperature of the heater 21 and the amount or time of opening of the valve 70 based on the detected values of the temperature sensor 90 and the humidity sensor 91 so that the studio A has a set temperature and a set humidity which are determined in advance. In such a case, the control unit 11 may store a program for performing such feedback control so that the feedback control is performed upon execution of the program.

Other than the above, for example, the respective proportions of the first lava plate 40 and the second lava plate 41 in the floor surface 50 of the studio A, the shape and size of the lava plate 33, and the placement pattern of the water supply pipe 22 and the heater 21 are not limited to those described above. Moreover, the layered structure 20 of the steam supply unit 10 may include other additional layers, as long as the layered structure 20 at least has the layers 30 to 33 described above.

INDUSTRIAL APPLICABILITY

The present invention is useful for providing systems and methods for adjusting the atmosphere of studios wherein the growth of bacteria in a second lava sand layer, which would otherwise occur when adjusting the atmosphere of a studio by using a steam supply unit, can be suppressed.

REFERENCE SIGNS LIST

1 Atmosphere adjustment system
10 Steam supply unit
11 Control unit
20 Layered structure
21 Heater
22 Water supply pipe
30 First lava sand layer
31 Mineral layer
32 Second lava sand layer
33 Lava plate

What is claimed is:
1. A system for adjusting an atmosphere of an exercise studio, the system comprising:
   a steam supply unit which has a layered structure including a first lava sand layer, a mineral layer, a second lava sand layer and a lava plate, which are stacked in this order from the bottom, a heater provided under the first lava sand layer, and a water supply pipe provided between the first lava sand layer and the mineral layer; and a control unit which is able to adjust a temperature of the second lava sand layer at 60° C. or higher and 80° C. or lower by controlling at least one of an amount of water discharged through the water supply pipe or a temperature of the heater, wherein the steam supply unit is placed on a floor of a studio, and wherein the steam supply unit is configured to discharge water to the first lava sand layer through the water supply pipe and to allow the discharged water to evaporate with the heater so that resulting steam passes through the mineral layer, accumulates in the second lava sand layer, and is then discharged into the studio through the lava plate.

2. The system for adjusting an atmosphere of an exercise studio according to claim 1, wherein the lava plate of the steam supply unit has a first lava plate having relatively high air permeability and a second lava plate having relatively low air permeability.

3. The system for adjusting an atmosphere of an exercise studio according to claim 2, wherein the first lava plate and the second lava plate are each arranged so as to occupy an almost equal proportion of a floor surface of the studio.

4. The system for adjusting an atmosphere of an exercise studio according to claim 1, wherein the second lava sand layer is formed so as to be thicker than the first lava sand layer.

5. The system for adjusting an atmosphere of an exercise studio according to claim 1, wherein the second lava sand layer has a lower layer which is made of lava sand with relatively large particle sizes and an upper layer which is made of lava sand with relatively small particle sizes.

6. The system for adjusting an atmosphere of an exercise studio according to claim 1, wherein the second lava sand layer has a thickness of 5 mm or more and 15 mm or less.

7. The system for adjusting an atmosphere of an exercise studio according to claim 1, wherein the first lava sand layer has a lower layer which is made of lava sand with relatively small particle sizes and an upper layer which is made of lava sand with relatively large particle sizes.

8. The system for adjusting an atmosphere of an exercise studio according to claim 1, wherein a thickness ratio of the second lava sand layer to the lava plate is set to 1:2 or greater and 1:4 or smaller.

9. The system for adjusting an atmosphere of an exercise studio according to claim 1, wherein the mineral layer includes at least one kind of mineral selected from quartz, rose quartz, tourmaline, tortoiseshell, agate tiger's eye, malachite, rutile quartz, pyrite, amazonite, turquoise, lapis lazuli, tumbled rock, and tumbled hawk's eye.

10. The system for adjusting an atmosphere of an exercise studio according to claim 1, wherein the water supply pipe is arranged in a predetermined pattern across a surface of the floor of the studio and the heater is arranged directly under the water supply pipe.

11. A method for adjusting an atmosphere of an exercise studio, the method comprising:
    placing a steam supply unit on a floor of a studio, wherein the steam supply unit has a layered structure including a first lava sand layer, a mineral layer, a second lava sand layer and a lava plate, which are stacked in this order from the bottom, a heater provided under the first lava sand layer, and a water supply pipe provided between the first lava sand layer and the mineral layer;
    discharging water to the first lava sand layer through the water supply pipe;
    using the heater so that the discharged water evaporates; and
    allowing resulting steam to pass through the mineral layer, accumulate in the second lava sand layer, and thereafter be discharged into the studio through the lava plate, so as to adjust an atmosphere of the studio,
    wherein, in the adjustment, at least one of an amount of water discharged through the water supply pipe or a temperature of the heater is controlled so that the second lava sand layer is at a temperature of 60° C. or higher and 80° C. or lower.

* * * * *